United States Patent [19]

Shiokawa et al.

[11] Patent Number: 5,219,869
[45] Date of Patent: Jun. 15, 1993

[54] NITRO-SUBSTITUTED HETEROCYCLIC COMPOUNDS

[75] Inventors: Kozo Shiokawa, Kanagawa; Shinichi Tsuboi, Tokyo; Koichi Moriya, Tokyo; Yumi Hattori, Tokyo; Ikuro Honda, Tokyo; Katsuhiko Shibuya, Tokyo, all of Japan

[73] Assignee: Nihon Bayer Agrochem K.K., Tokyo, Japan

[21] Appl. No.: 943,950

[22] Filed: Sep. 11, 1992

Related U.S. Application Data

[60] Continuation of Ser. No. 760,412, Sep. 16, 1991, abandoned, which is a division of Ser. No. 518,684, May 3, 1990, Pat. No. 5,081,132.

[30] Foreign Application Priority Data

May 17, 1989 [JP] Japan .................. 1-121366

[51] Int. Cl.$^5$ .................. A01N 43/78; C07D 417/12; C07D 417/14
[52] U.S. Cl. .................. 514/333; 514/340; 514/341; 514/342; 514/365; 514/369; 514/370; 546/256; 546/275; 546/276; 546/279; 546/280; 548/184; 548/191; 548/202; 548/204; 548/205
[58] Field of Search .............. 514/333, 340, 341, 342, 514/365, 369, 370; 546/256, 276, 275, 279, 280; 548/202, 184, 191, 204, 205

[56] References Cited

U.S. PATENT DOCUMENTS

| | | | |
|---|---|---|---|
| 4,876,263 | 10/1989 | Shiokawa et al. | 514/338 |
| 5,023,259 | 6/1991 | Gsell | 514/256 |
| 5,084,459 | 1/1992 | Uneme et al. | 514/256 |

FOREIGN PATENT DOCUMENTS

| | | |
|---|---|---|
| 0248348 | 12/1987 | European Pat. Off. |
| 0366085 | 5/1990 | European Pat. Off. |
| 0407594 | 1/1991 | European Pat. Off. |
| 2139042 | 2/1972 | Fed. Rep. of Germany |

OTHER PUBLICATIONS

39286d: "Insecticidal and fungicidal activites of 4-N--substituted ...", Chem. Abst., vol. 79, 1973, p. 92 (Kurilenko et al.).
39197a: Tret'Yakova et al., "Physiological activity of some amino ... ", Chem. Abst., vol. 79, p. 83; 1973.
53195v: Sone et al., "Reaction of 1-nitro-2,2-bis(methylthio)ethylene ... ", Chem. Abst., vol. 87, 1977, p. 464.
76205r: V. J. Ram, "Thiophenes, pyrazolothiophenes and pyrimidothiophenes ... ", Che. Abst., vol. 92, 1980; p. 650.
Chem. Ber., vol. 119, pp. 2208-2219 (1968).
J. Chem. Soc. Perkin Trans. I, 1979, pp. 2361-2363.
Journal of Heterocyclic Chem., vol. 17, p. 1413 (1980).
Heterocycles 15, p. 437 (1980).

Primary Examiner—Patricia L. Morris
Attorney, Agent, or Firm—Sprung Horn Kramer & Woods

[57] ABSTRACT

Insecticidal nitro-substituted heterocyclic compounds of the formula

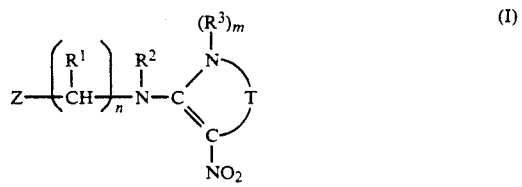

(I)

wherein
$R^1$ represents hydrogen, cyano or $C_{1-4}$ alkyl,
m represents 0 or 1,
n represents 0 or 1,
$R^2$ represents hydrogen or $C_{1-4}$ alkyl,
$R^3$ represents hydrogen, $C_{1-6}$ alkyl optionally substituted substituted by cyano, halogen or $C_{1-4}$ alkoxy, $C_{3-4}$ alkenyl, $C_{3-4}$ alkynyl, optionally substituted phenyl, optionally substituted benzyl or optionally substituted heterocyclic-methyl,
T represents an optionally substituted two- or three-membered divalent or trivalent chain comprising hetero atoms and/or carbon atom, and
A represents optionally substituted phenyl or an optionally substituted five- or six-membered heterocyclic radical comprising at least one hetero atom selected from the group consisting of N, O and S.

5 Claims, No Drawings

NITRO-SUBSTITUTED HETEROCYCLIC COMPOUNDS

This is a continuation of application Ser. No. 760,412, filed Sep. 16, 1991, now abandoned, which is a division of application Ser. No. 518,684, filed May 3, 1990, now U.S. Pat. No. 5,081,132.

The present invention relates to novel nitro-substituted heterocyclic compounds, to processes for their preparation and to their use as insecticides.

A number of nitro-substituted heterocyclic compounds is already known from literature, for example
A) Chem. Ber., Vol. 119, pp. 2208–2219 (1968);
B) J. Chem. Soc. Perkin Trans. I, 1979, pp. 2361–2363;
C) Journal of Heterocyclic Chem., Vol. 17, p. 1413 (1980);
D) Heterocycles 15, p. 437 (1980)

Typical examples of such compounds are the following:

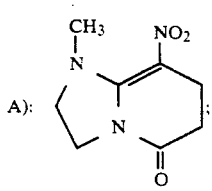

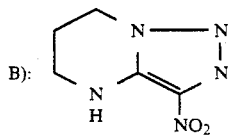

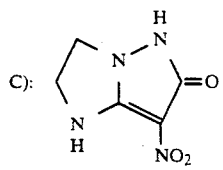

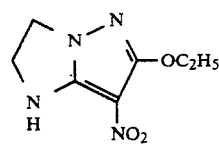

and

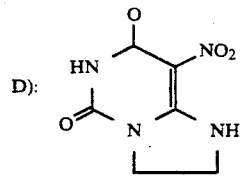

Furthermore, it has already been disclosed that a certain nitro-substituted heterocyclic compound has insecticidal properties (see Japanese Patent Laid-open No. 3184/1989).

There have now been found novel nitro-substituted heterocyclic compounds of the formula (I)

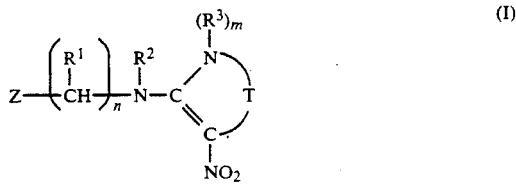

wherein
$R^1$ represents hydrogen, cyano or $C_{1-4}$ alkyl, group,
m represents 0 or 1,
n represents 0 or 1,
$R^2$ represents hydrogen or $C_{1-4}$ alkyl,
$R^3$ represents hydrogen; $C_{1-6}$ alkyl optionally substituted by cyano, halogen or $C_{1-4}$ alkoxy, $C_{3-4}$ alkenyl, $C_{3-4}$ alkynyl, optionally substituted phenyl, optionally substituted benzyl or optionally substituted heterocyclic-methyl,
T represents an optionally substituted two- or three-membered divalent or trivalent chain comprising hetero atoms and/or carbon atoms, and
Z represents optionally substituted phenyl or an optionally substituted five- or six-membered heterocyclic radical comprising at least one hetero atom selected from the group consisting of N, O and S.

The compounds of the formula (I) can be obtained as follows:

a): (when m is 1 and T is

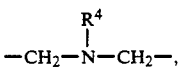

wherein $R^4$ is $C_{1-4}$ alkyl, $C_{3-7}$ cycloalkyl, benzyl optionally substituted by halogen, phenyl optionally substituted by halogen or $C_{1-6}$ alkyl, or 2-chloro-5-pyridylmethyl),
compounds of the formula (II)

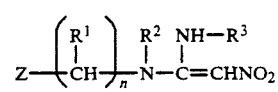

wherein $R^1$, n, $R^2$ and $R^3$ have the same meanings as mentioned before,
are reacted with compounds of the formula (III)

$$NH_2-R^4 \quad\quad (III)$$

wherein $R^4$ has the same meaning as mentioned before, in the presence of formaldehyde,
and if appropriate, in the presence of inert solvents, b): (when m is 1 and T is

wherein — means linkage with the nitrogen atom),
the aforementioned compounds of the formula (II) are reacted with chlorocarbonylsulphenyl chloride in the presence of inert solvents and if appropriate in the presence of an acid binder, c): (when m is 1 and T is $$\underset{\|}{\overset{O}{+C-CH_2-CH_2-,}}$$

wherein the symbol —is the same as mentioned above), the aforementioned compounds of the formula (II) are reacted with compounds of the formula (IV)

$$CH_2=CHCOOR \qquad (IV)$$

wherein R represents a lower alkyl group, in the presence of inert solvents, d): (when m is 1 and T is $$\underset{\|}{\overset{O}{+C-CH-CH-,}}$$

wherein the symbol —is the same as mentioned above), the aforementioned compounds of the formula (II) are reacted with compounds of the formula (V)

$$HC\equiv CCOOR \qquad (V)$$

wherein R has the same meaning as mentioned before, in the presence of inert solvents, e): (when m is 1 and T is $$\underset{\|}{\overset{O}{+C-CH-\overset{COOR}{\underset{|}{C}}-}},$$

wherein the symbol —is the same as mentioned above), the aforementioned compounds of the formula (II) are reacted with compounds of the formula (VI)

$$ROOCC\equiv CCOOR \qquad (VI)$$

wherein R has the same meaning as mentioned above, in the presence of inert solvents, f): (when m is 1 and T is $$+S-\underset{\underset{N-Q}{|}}{C-},$$

wherein the symbol —is the same as mentioned above and Q is $C_{1-4}$ alkyl or $C_{1-4}$ alkoxycarbonylimino), compounds of the formula (VII)

$$Z-(\underset{\underset{}{|}}{\overset{R^1}{CH}})_n-\underset{\underset{}{}}{N}-\underset{\underset{S}{|}}{C}=C\underset{\diagdown}{\overset{\diagup}{\underset{}{}}}\overset{R^2}{\underset{}{}}\overset{NH-R^3}{\underset{}{|}}\overset{NO_2}{\underset{}{}} \qquad (VII)$$
$$\phantom{Z-(CH)_n-N-C=C}C-NH-Q$$

wherein $R^1$, n, $R^2$, $R^3$, Z and Q have the same meanings as mentioned above, are oxidized in the presence of inert solvent, g): (when m is 1 and T is —N=N—), the aforementioned compounds of the formula (II) are reacted with 4-chlorobenzenesulfonylazide in the presence of inert solvents, h): (when m is 1 and T is $$\underset{\|}{\overset{O}{-C}}-\underset{\|}{\overset{O}{C}}-),$$

the aforementioned compounds of the formula (II) are reacted with oxazolyl chloride in the presence of inert solvents and if appropriate in the presence of an acid binder, i): (when m is 1 and T is $$\underset{\|}{\overset{O}{-C}}-NH-\underset{\|}{\overset{O}{C}}-),$$

the aforementioned compounds of the formula (II) are reacted with chlorocarbonyl isocyanate in the presence of inert solvents and if appropriate in the presence of an acid binder, j): (when m is 1 and T is $$+CH_2-CH_2-\underset{\underset{}{|}}{\overset{NH}{C}}-,$$

wherein the symbol —has the same meaning as mentioned before), the aforementioned compounds of the formula (II) are reacted with halopropionitrile of the formula (VIII)

$$Hal-CH_2CH_2CN \qquad (VIII)$$

wherein Hal means halogen, in the presence of inert solvents and if appropriate in the presence of an acid binder, k): (when m is 1 and T is $$+CH-\underset{\underset{}{|}}{\overset{R^4}{C}}-,$$

wherein the symbol —has the same meaning as mentioned before and $R^4$ represents hydrogen, $C_{1-4}$ alkyl or $C_{1-4}$ alkoxy), the aforementioned compounds of the formula (II) are reacted with compounds of the formula (IX)

$$Hal-CH_2-\underset{\|}{\overset{O}{C}}-R^4 \qquad (IX)$$

wherein $R^4$ and Hal have the same meanings as mentioned before, in the presence of inert solvents and if appropriate in the presence of an acid binder, l): (when m is 1, $R^3$ is hydrogen atom, and T is —CH=CH—), compounds of the formula (X)

$$Z-(\overset{R^1}{\underset{\underset{}{|}}{CH}})_n-\underset{\underset{CHNO_2}{|}}{\overset{R^2}{\underset{|}{N}}}\underset{}{\diagdown}NH-CH_2CH(OR)_2 \qquad (X)$$

wherein $R^1$, n, $R^2$, Z and R have the same meanings as mentioned before, are reacted with acid in the presence of inert solvents, m): (when m is 1, $R^3$ has the same meaning as defined before, excluding hydrogen, and T is —CH=CH—, wherein R³ is denoted as R⁵), compounds of the formula (II)

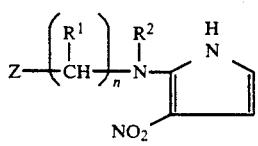

(II)

wherein R¹, n, R² and Z have the same meanings as mentioned before,
are reacted with compounds of the formula (XI)

R⁵—Hal    (XI)

wherein R⁵ and Hal have the same meanings as mentioned before,
in the presence of inert solvents and if appropriate in the presence of an acid binder,
or n): compounds of the formula (XII)

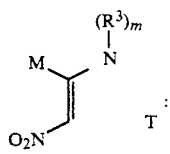

(XII)

wherein m, R³ and T have the same meanings as mentioned before and M means methylthio or halogen,
are reacted with compounds of the formula (XIII)

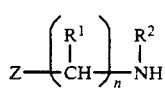

(XIII)

wherein R¹, n, R² and Z have the same meanings as mentioned before,
in the presence of inert solvents and if appropriate in the presence of an acid binder.

The novel nitro-substituted heterocyclic compounds exhibit powerful insecticidal properties.

Surprisingly, the nitro-substituted heterocyclic compounds according to the invention exhibit a substantially greater insecticidal activity than those known from the aforementioned prior art.

Among the nitro-substituted heterocyclic compounds according to the invention, of the formula (I), preferred compounds are those in which
R¹ represents hydrogen, cyano group or methyl,
m represents 0 or 1,
n represents 0 or 1,
R² represents hydrogen or methyl,
R³ represents hydrogen, methyl, ethyl, propyl, butyl, chloro- or fluoro-substituted $C_{1-2}$ alkyl, alkoxyalkyl having a total of from 2 to 4 carbon atoms, cyano-substituted $C_{1-2}$ alkyl, allyl, propargyl, phenyl which may be substituted by $C_{1-4}$ alkyl or halogen, benzyl
which may be substituted by halogen, or pyridylmethyl which may be substituted by halogen, T represents optionally substituted two- or three-membered divalent or trivalent chain comprising nitrogen or sulfur and carbon atoms, wherein said optional substituent may include $C_{1-4}$ alkyl,
$C_{2-4}$ alkenyl, $C_{2-4}$ alkynyl, halogen, $C_{3-7}$-cycloalkyl,
nitro, oxo, thioxo, phenyl optionally substituted by halogen or $C_{1-6}$ alkyl, benzyl optionally substituted by halogen, $C_{1-4}$ alkylimino, $C_{1-4}$ alkoxycarbonylimino,
substituted amino, $C_{1-2}$ alkyl optionally substituted by cyano, $C_{2-4}$ (in total) alkoxyalkyl, 2-chloro-5-pyridylmethyl,
$C_{1-4}$ alkoxy, imino, or $C_{1-4}$ alkoxycarbonyl, and 2 represents phenyl optionally substituted by halogen or cyano, a five-membered heterocyclic group optionally substituted by halogen or $C_{1-4}$ alkyl, the heterocyclic group comprising one or two nitrogen atoms and an oxygen atom or sulfur atom, or a six-membered heterocyclic group optionally substituted by halogen or $C_{1-4}$ alkyl, the heterocyclic group comprising one or two nitrogen atoms.

Very particularly preferred nitro-substituted heterocyclic compounds of formula (I) are those in which
R¹ represents hydrogen, or methyl,
m represents 0 or 1,
n represents 0 or 1,
R² represents hydrogen or methyl,
R³ represents hydrogen, methyl, fluoro-substituted $C_{1-2}$ alkyl, 2-methoxyethyl, 2-cyanoethyl, allyl, propargyl, phenyl, benzyl optionally substituted by chlorine, or 2-chloro-5-pyridylmethyl,
T represents optionally substituted two- or three-membered divalent or trivalent chain comprising a nitrogen atom or sulfur atom and carbon atoms, wherein said optional substituent may include methyl, ethyl, propyl, isopropyl, butyl, allyl, propargyl, chlorine, cyclohexyl, nitro, oxo, thioxo, phenyl optionally substituted by chlorine or $C_{1-4}$ alkyl, benzyl optionally substituted by chlorine or fluorine, $C_{1-2}$ alkylimino, $C_{1-2}$ alkoxy-carbonylimino, N-methyl-N-(2-chloro-5-pyridyl)amino, α-methyl-4-chlorobenzylamino, 2-ethoxyethylamino, cyanomethyl, 2-methoxyethyl, 2-chloro-5-pyridylmethyl, $C_{1-2}$ alkoxy, imino, or ethoxycarbonyl, and Z represents phenyl optionally substituted by chlorine or cyano, thiazolyl optionally substituted by chlorine or methyl, or pyridyl optionally substituted by chlorine or methyl.

Specifically, the following compounds may be mentioned:
2-[N-(2-chloro-5-pyridylmethyl)-N-methylamino]-3-nitropyridine,
2-[N-(2-chloro-5-pyridylmethyl)-N-methylamino]-3-nitropyrrole,
2-[N-(2-chloro-5-pyridylmethyl)-N-methylamino]-1-methyl-3-nitropyrrole,
4-(2-chloro-5-pyridylmethylamino)-1,3-dimethyl-5-nitro-1,2,3,6-tetrahydropyrimidine,
4-[N-(2-chloro-5-pyridylmethyl)-N-methylamino]-3-methyl-5-nitro-2-thiazolone, and
4-(2-chloro-5-pyridylmethylamino)-1-dodecyl-3-methyl-5-nitro-1,2,3,6-tetrahydropyrimidine.

In the process a), if use is made, as starting material, of 1-(2-chloro-5-pyridylmethylamino)-1-methylamino-2-nitroethylene and methylamine, for example, the reaction can be expressed as follows:

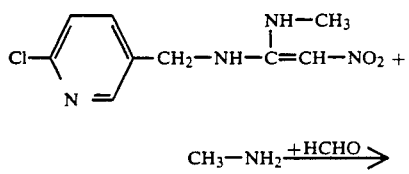

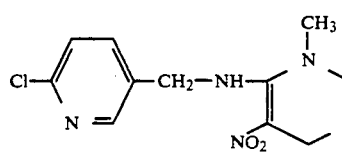

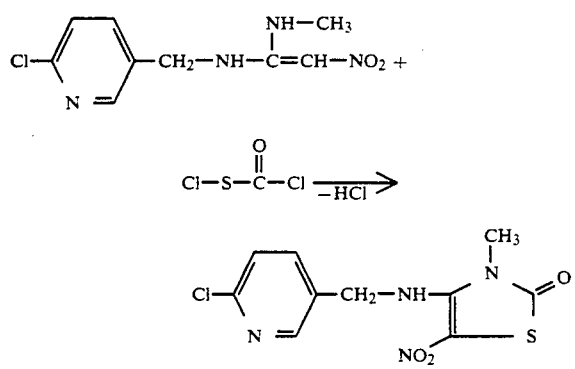

In the process b), if use is made, as starting material, of 1-(2-chloro-5-pyridylmethylamino)-1-methylamino-2-nitroethylene and chlorocarbonylsulfenyl chloride, for example, the reaction can be expressed as follows:

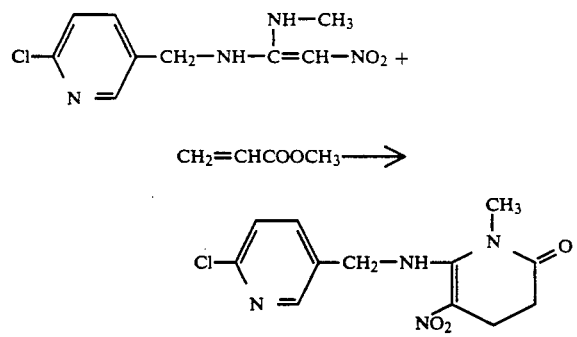

In the process c), if use is made, as starting material, of 1-(2-chloro-5-pyridylmethylamino)-1-methylamino-2-nitroethylene and methyl acrylate, for example, the reaction can be expressed as follows:

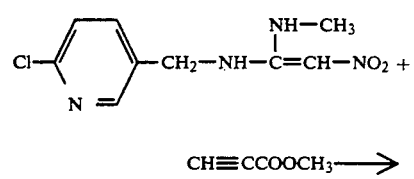

In the process d), if use is made, as starting material, of 1-(2-chloro-5-pyridylmethylamino)-1-methylamino-2-nitroethylene and propynoic acid methyl ester, for example, the reaction can be expressed as follows:

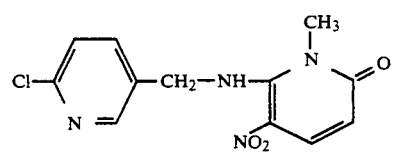

In the process e), if use is made, as starting material, of 1-(2-chloro-5-pyridylmethylamino)-1-methylamino-2-nitroethylene and dimethyl butyne (2) dioic acid, for example, the reaction can be expressed as follows:

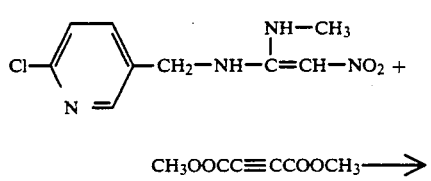

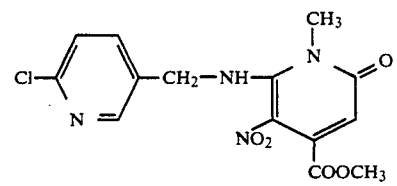

In the process f), if use is made, as starting material, of 3-(2-chloro-5-pyridylmethylamino)-3-methylamino-2-nitrothioacrylic acid ethoxycarbonylimide and bromine, for example, the reaction can be expressed as follows:

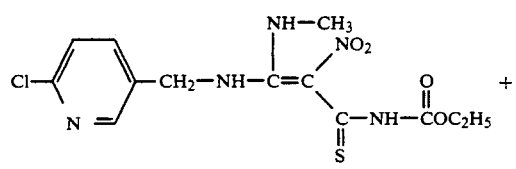

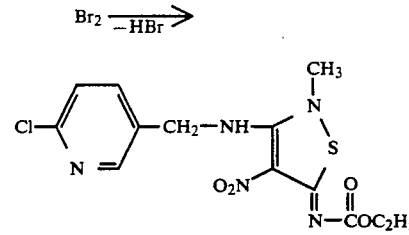

In the process g), if use is made, as starting material, of 1-(2-chloro-5-pyridylmethylamino)-1-methylamino-2-nitroethylene and 4-chlorobenzene sulfonylazide, for example, the reaction can be expressed as follows:

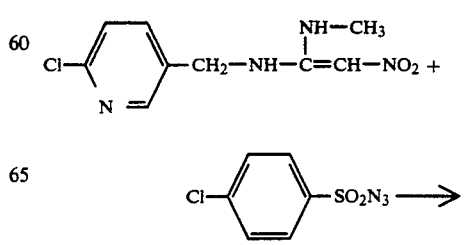

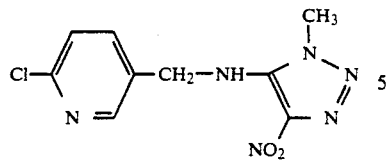

In the process h), if use is made, as starting material, of 1-(2-chloro-5-pyridylmethylamino)-1-methylamino-2-nitroethylene and oxalyl chloride, for example, the reaction can be expressed as follows:

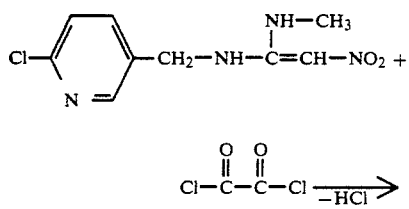

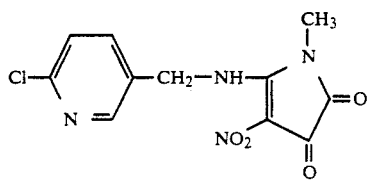

In the process i), if use is made, as starting material, of 1-(2-chloro-5-pyridylmethylamino)-1-methylamino-2-nitroethylene and chloro-carbonyl isocyanate, for example, the reaction can be expressed as follows:

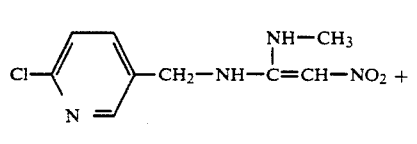

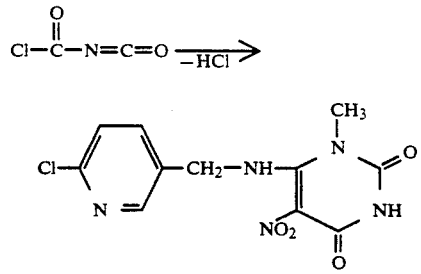

In the process j), if use is made, as starting material, of 1-(2-chloro-5-pyridylmethylamino)-1-methylamino-2-nitroethylene and 3-chloropropionitrile, for example, the reaction can be expressed as follows:

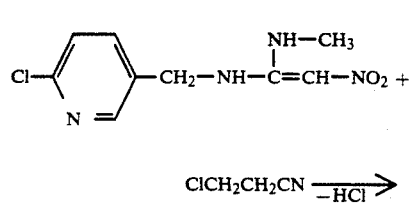

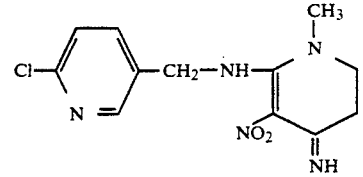

In the process k), if use is made, as starting material, of 1-amino-1-(N-methyl-2-chloro-5-pyridylmethylamino)-2-nitroethylene and chloroacetone, for example, the reaction can be expressed as follows:

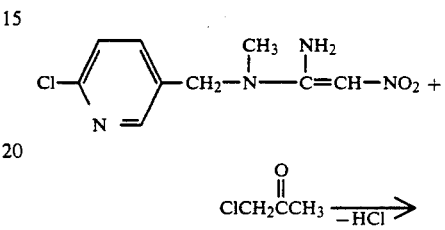

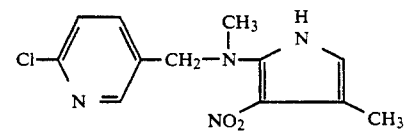

In the process l), if use is made, as starting material, of 1-(2-chloro-5-pyridylmethylamino)-1-(2,2-diethoxyethylamino)-2-nitroethylene and concentrated hydrochloric acid, for example, the reaction can be expressed as follows:

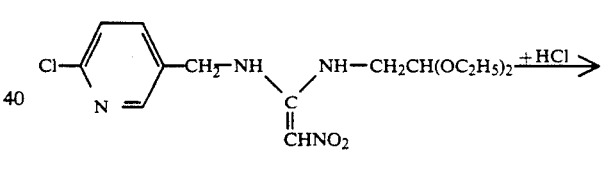

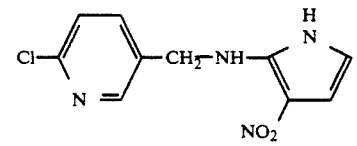

In the process m), if use is made, as starting material, of 2-[N-(2-chloro-5-pyridylmethyl)-N-methylamino]-3-nitropyrrol and dimethyl sulfate as alkylating agent, for example, the reaction can be expressed as follows:

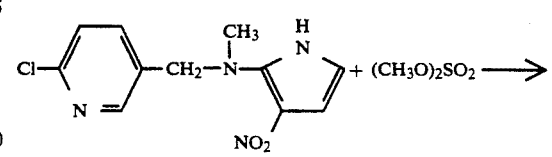

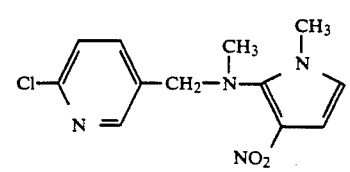

In the process n), if use is made, as starting material, of 2-chloro-3-nitropyridine and N-(2-chloro-5-pyridylmethyl)-methylamine, for example, the reaction can be expressed as follows:

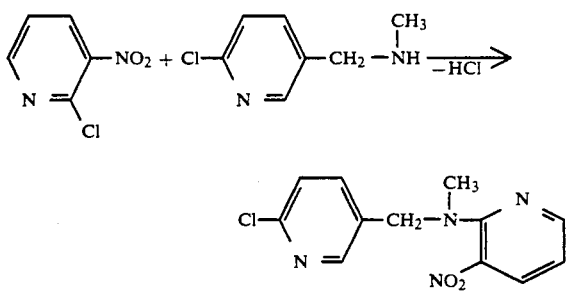

In the processes a), b), c), d), e), g), h), i), j) and k), the compounds of the formula (II) as a starting material mean those based on the aforementioned definitions of $R^1$, n, $R^2$ and $R^3$.

In the formula (II), $R^1$, n, $R^2$ and $R^3$ preferably have the same meanings as already given above for the formula (I) as preferred.

The compounds of the formula (II) include known compounds. (see Japanese Patent Laid-open 65047/1984 or EP-OS 302,389)

As example, there may be mentioned 1-(2-chloro-5-pyridylmethylamino)-1-methylamino-2-nitroethylene.

In the process a), the compounds of the formula (III) as a starting material mean those based on the aforementioned definition of $R^4$.

In the formula (III), $R^4$ preferably means methyl, ethyl, propyl, isopropyl, butyl, cyclohexyl, benzyl optionally substituted by chlorine or fluorine, or 2-chloro-5-pyridylmethyl.

The compounds of the formula (III) are for the most part well-known as primary amines in the field of organic chemistry. As examples, there may be mentioned: methylamine, ethylamine, propylamine, isopropylamine, cyclohexylamine and benzylamine, etc.

In the process c), the compounds of the formula (IV) as a starting material mean those based on the aforementioned definition of R.

In the formula (IV), R preferably means $C_{1-4}$ alkyl, such as methyl, ethyl, propyl, isopropyl, butyl, isobutyl, sec-butyl and tert-butyl.

The compounds of the formula (IV) are well-known in the field of organic chemistry. As example there may be methyl acrylate.

In the process d), the compounds of the formula (V) as a starting material mean ones based on the aforementioned definition of R.

The compounds of the formula (V) are well-known in the field of organic chemistry. As example there may be propynoic acid methyl ester.

In the process e), the compounds of the formula (VI) as a starting material mean ones based on the aforementioned definition of R.

The compounds of the formula (VI) are well-known in the field of organic chemistry. As example there may be butyne (2) dioic acid dimethyl.

In the process f), the compounds of the formula (VII) as a starting material mean ones based on the aforementioned definitions of $R^1$, n, $R^2$, $R^3$, Z or Q.

In the formula (VII), $R^1$, n, $R^2$, $R^3$ and Z preferably have the same meanings as already given above for the formula (I) as the preferred. Q preferably represents methyl, ethyl, methoxycarbonylimino or ethoxycarbonylimino.

The compounds of the formula (VII) can be obtained by a process comprising reacting the aforementioned compounds of the formula (II) with compounds of the formula (XIV)

$$Q-NCS \qquad (XIV)$$

wherein Q has the same meaning as mentioned before, in the presence of inert solvents.

The above compounds of the formula (XIV) are known, and as example there is ethoxycarbonyl isothiocyanate.

In the process j), the compounds of the formula (VIII) as a starting material mean those based on the aforementioned definition of Hal.

In the formula (VIII), Hal preferably represents chlorine, bromine or iodine.

The compounds of the formula (VIII) are well-known, and as example there may be mentioned 3-chloropropiononitrile.

In the process k), the compounds of the formula (IX) as a starting material mean those based on the aforementioned definitions of $R^4$ and Hal.

The compounds of the formula (IX) are well-known in the field of organic chemistry, and as examples there are chloroacetone and methyl chloroacetate.

In the process l), the compounds of the formula (X) as a starting material means those based on the aforementioned definitions of $R^1$, n, $R^2$, Z and R.

In the formula (X), $R^1$, n, $R^2$, Z and R preferably have the same meanings as already given above.

As examples there may be mentioned:
1-(2-chloro-5-pyridylmethylamino)-1-(2,2-diethoxyethylamino)-2-nitroethylene, and
1-[N-methyl-N-(2-chloro-5-pyridylmethyl)amino]-1-(2,2-diethoxydiethylamino)-2-nitroethylene.

In the process m), the compounds of the formula (XI) as a starting material mean those based on the aforementioned definitions of $R^5$ and Hal.

In the formula (XI), $R^5$ preferably represents definitions other than hydrogen of the aforementioned preferred definitions of $R^3$, and Hal preferably has the same meaning as already given above, As examples, an alkylating agent such as chloromethane, iodomethane, etc., can be employed and, besides the compounds of the formula (XI), dimethyl sulfate and diethyl sulfate which are well-known as alkylating agents may be used in place of the compounds of the formula (XI).

In the process n), the compounds of the formula (XII) as a starting material mean those based on the aforementioned definitions of $R^3$, T and M.

In the formula (XII), $R^3$ and T preferably have the same meanings as already given above, and M preferably represents methylthio, chlorine or bromine.

As examples of the compounds of the formula (XII), there may be mentioned
2-chloro-3-nitropyridine,
1,3-dimethyl-4-methylthio-5-nitro-1,2,3,6-tetrahydropyrimidine,
2-methylthio-3-nitro-1-phenylpyrrol-4,5-dione, and
3-methyl-4-methylthio-5-nitrothiazolone.

The above 1,3-di-substituted-4-methylthio-5-nitro-1,2,3,6-tetrahydropyrimidines can be obtained by a process comprising reacting compounds of the formula (XV)

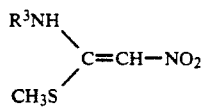

wherein R³ has the same meaning as mentioned before, with the aforementioned compounds of the formula (III) in the presence of formaldehyde.

The compounds of the formula (XV) include known compounds described for instance in Japanese Patent Laid-open 17557/1986 and as example there may be mentioned N-methyl-1-methylthio-2-nitroethene amine. Furthermore, 2-anilino-2-methyltho-1-nitroethylene described in Journal F. prakt. Chemie, Band 319, Heft 1, 1977, S 149-158 may be employed.

In the aforementioned examples of the compounds of the formula (XII), 2-methylthio-3-nitro-1-phenylpyrrol-4,5-dione is a known compound described in the aforecited Journal F. prakt. Chemie, Band 319, Heft 1, 1977, S 149-158, and 3-substituted-4-methylthio-5-nitrothiazolones can be obtained by a process comprising reacting the compounds of the formula (XV) with chlorocarbonylsulfenylchloride.

In the process n), the compounds of the formula (XIII) as a starting material mean those based on the aforementioned definitions of R¹, n, R² and Z.

In the formula (XIII), R¹, n, R² and Z preferably have the same meanings as already given above.

The compounds of the formula (XIII) are known (see EP-OS 302,389), and as examples there may be mentioned:
N-(2-chloro-5-pyridylmethyl)-methylamine and
N-(2-chloro-5-thiazolylmethyl)-methylamine.

In carrying out the process (a) mentioned above, use may be made, as suitable diluent, of any inert solvents.

Examples of such diluents are water; aliphatic, cycloaliphatic and aromatic, optionally chlorinated, hydrocarbons, such as hexane, cyclohexane, petroleum ether, ligroin, benzene, toluene, xylene, methylene chloride, chloroform, carbon tetrachloride, ethylene chloride, trichloroethylene, chlorobenzene, and the like; ethers such as diethyl ether, methyl ethyl ether, di-isopropyl ether, dibutyl ether, propylene oxide, dioxane, tetrahydrofuran and the like; nitriles such as acetonitrile, propionitrile, acrylonitrile and the like; alcohols such as methanol, ethanol, iso-propanol, butanol, ethylene glycol and the like; esters such as ethyl acetate, amyl acetate and the like; acid amides such as dimethyl formamide, dimethyl acetamide and the like; and sulfones and sulfoxides such as dimethyl sulfoxide, sulfolane and the like; and bases, for example, pyridine, etc.

In the process a), the reaction temperature can be varied within a wide range. In general, the reaction is carried out at a temperature of about 0° to about 150° C., preferably about 60° to about 100° C. In general, the reaction is allowed to proceed under normal pressure, although it is also possible to employ a higher or lower pressure.

When the process a) according to the invention is carried out, use is made, for instance, of 1 to 1.2 moles, preferably 1 to about 1.1 moles of the compounds of the formula (III) per mole of the compounds of the formula (II) for example, in the presence of about 2.2 moles of formaldehyde and ethanol to obtain the desired compounds of the formula (I).

In carrying out the process b), use is made, as suitable diluent, of any inert solvents such as those exemplified in the above-mentioned process a).

The above-mentioned process b) may be carried out in the presence of an acid binders such as, for example, hydroxide, hydride, carbonate bicarbonate, and alcoholate of alkali metal that are conventional acid binders, and tertiary amines such as, for example, triethylamine, diethyl aniline, pyridine, and the like.

In the process b), the reaction temperature can be varied within a wide range. In general, the reaction is carried out at a temperature of about 0° to about 150° C., preferably about 10° to about 50° C. In general, the reaction is allowed to proceed under normal pressure, although it is also possible to employ a higher or lower pressure.

When the process b) according to the present invention is carried out, use is made, for instance, of 1 to 1.2 moles, preferably from 1 to about 1.1 moles of chlorocarbonylsulfenyl chloride per 1 mole of the compounds of the formula (II) for example to obtain the desired compounds of the formula (I).

The process b) can be carried out according to the procedures disclosed by J. F. Pract. Chem. vol. 319, page 149.

In carrying out the process c), use is made, as suitable diluent, of any inert solvents such as those exemplified in the above-mentioned process a).

In the process c), the reaction temperature can be varied within a wide range. In general, the reaction is carried out at a temperature of about 0° to about 150° C., preferably about 50° to about 100° C. In general, the reaction is allowed to proceed under normal pressure, although it is also possible to employ a higher or lower pressure.

When the process c) according to the invention is carried out, use is made, for instance, of 1 to 1.2 moles, preferably from 1 to about 1.1 moles of the compounds of the formula (IV) per mole of the compounds of the formula (II) for example to obtain the desired compounds of the formula (I).

In carrying out the process d), use is made, as suitable diluent, of any inert solvents such as those exemplified in the above-mentioned process a).

In the process d), the reaction temperature can be varied within a wide range. In general, the reaction is carried out at a temperature of about 0° to about 150° C., preferably about 50° to about 100° C. In general, the reaction is allowed to proceed under normal pressure, although it is also possible to employ a higher or lower pressure.

When the process d) according to the present invention is carried out, use is made, for instance, of 1 to 1.2 moles, preferably from 1 to about 1.1 moles of the compounds of the formula (V) per mole of the compounds of the formula (II) for example to obtain the desired compound represented by the formula (I).

In carrying out the process e), use is made, as suitable diluent, of any inert solvents such as those exemplified in the above-mentioned process a).

In the process e), the reaction temperature can be varied within a wide range. In general, the reaction is carried out at a temperature of about 0° to about 150° C., preferably about 50° to about 100° C. In general, the reaction is allowed to proceed under normal pressure, although it is also possible to employ a higher or lower pressure.

When the process e) according to the present invention is carried out, use is made, for instance, of 1 to 1.2 moles, preferably from 1 to about 1.1 moles of the compounds of the formula (VI) per mole of the compounds of the formula (II) for example to obtain the desired compounds of the formula (I).

The above-mentioned processes c), d), and e) can be carried out according to the known Michael reaction.

In carrying out the process f), use is made, as suitable diluent, of any inert solvents such as those exemplified in the above-mentioned process a).

In the process f), the reaction temperature can be varied within a wide range. In general, the reaction is carried out at a temperature of about 0° to about 100° C., preferably about 20° to about 60° C. In general, the reaction is allowed to proceed under normal pressure, although it is also possible to employ a higher or lower pressure.

The process f) according to the present invention can be carried out according to the process disclosed by Tetrahedron, vol. 33, page 1057; vol. 37, page 1470 and Indian J. Chem., 15B, 1977, pages 886–889.

In carrying out the process g), use is made, as suitable diluent, of any inert solvents such as those exemplified in the above-mentioned process a).

In the process g), the reaction temperature can be varied within a wide range. In general, the reaction is carried out at a temperature of about 0° to about 150° C., preferably about 50° to about 80° C. In general, the reaction is allowed to proceed under normal pressure, although it is also possible to employ a higher or lower pressure.

When the process g) according to the invention is carried out, use is made, for instance, of 1 to 1.2 moles, preferably from 1 to about 1.1 moles of 4-chlorobenzenesulfonylazide per mole of the compounds of the formula (II) for example to obtain the desired compounds of the formula (I).

The above-mentioned process g) can be carried out according to the process disclosed by J. Chem. Soc., Perkin I trans. 1979, pages 2361–2363.

In carrying out the process h), use is made, as suitable diluent, of any inert solvents such as those exemplified in the above-mentioned process a).

The above-mentioned process h) may be carried out in the presence of an acid binder such as exemplified in the process b).

In the process h), the reaction temperature can be varied within a wide range. In general, the reaction is carried out at a temperature of about −20° C. to about 100° C., preferably about 0° C. to about 50° C. In general, the reaction is allowed to proceed under normal pressure, although it is also possible to employ a higher or lower pressure.

When the process h) according to the invention is carried out, use is made, for instance, of 1 to 1.2 moles, preferably from 1 to about 1.1 moles of oxalyl chloride per mole of the compounds of the formula (II) for example to obtain the desired compounds of the formula (I).

The above-mentioned process h) can be carried out according to a process similar to that disclosed in the above-mentioned J. F. Pract. Chem., vol. 319, page 149.

In carrying out the process i), use is made, as suitable diluent, of any inert solvents such as those exemplified in the above-mentioned process a).

The above mentioned process i) may be carried out in the presence of an acid binder such as exemplified in the process b).

In the process i), the reaction temperature can be varied within a wide range. In general, the reaction is carried out at a temperature of about −20° C. to about 100° C., preferably about 0° C. to about 50° C. In general, the reaction is allowed to proceed under normal pressure, although it is also possible to employ a higher or lower pressure.

When the process i) according to the invention is carried out, use is made, for instance, of 1 to 1.2 moles, preferably from 1 to about 1.1 moles of chlorocarbonyl isocyanate per mole of the compounds of the formula (II) for example to obtain the desired compounds of the formula (I).

In carrying out the process j), use is made, as suitable diluent, of any inert solvents such as those exemplified in the above-mentioned process a).

The above mentioned process j) may be carried out in the presence of an acid binder such as exemplified in the process b).

In the process j), the reaction temperature can be varied within a wide range. In general, the reaction is carried out at a temperature of about 0° to about 100° C., preferably about 20° C. to about 50° C. In general, the reaction is allowed to proceed under normal pressure, although it is also possible to employ a higher or lower pressure.

When the process j) according to the invention is carried out, use is made, for instance, of about 1 to about 1.2 moles, preferably 1 to 1.1 moles of the compounds of the formula (VIII) per mole of the formula (II) for example to obtain the desired compounds of the formula (I).

In carrying out the process k), use is made, as suitable diluent, of any inert solvents such as those exemplified in the above-mentioned process a).

The above mentioned process k) may be carried out in the presence of an acid binder such as exemplified in the process b).

In the process k), the reaction temperature can be varied within a wide range. In general, the reaction is carried out at a temperature of about −20° C. to about 80° C., preferably from about 0° C. to about 50° C. In general, the reaction is allowed to proceed under normal pressure, although it is also possible to employ a higher or lower pressure.

When the process k) according to the invention is carried out, use is made, for instance, of about 1 to about 1.2 moles, preferably from about 1 to 1.1 moles of the compounds of the formula (IX) per mole of the compounds of the formula (II) for example to obtain the desired compounds of the formula (I).

The processes i), j) and k) mentioned above can be carried out in accordance with a process disclosed by Japanese Patent Application Disclosure No. 3184-1989.

In carrying out the process l), use is made, as suitable diluent, of any inert solvents such as those exemplified in the above-mentioned process a).

In the process l), the reaction temperature can be varied within a wide range. In general, the reaction is carried out at a temperature of about 0° to about 150° C., preferably about 50° to about 80° C. In general, the reaction is allowed to proceed under normal pressure, although it is also possible to employ a higher or lower pressure.

In carrying out the process m), use is made, as suitable diluent, of any inert solvents such as those exemplified in the above-mentioned process a).

The above mentioned process m) may be carried out in the presence of an acid binder such as exemplified in the process b).

In the process m), the reaction temperature can be varied within a wide range. In general, the reaction is carried out at a temperature of about −20° C. to about 100° C., preferably about 0° C. to about 50° C. In general, the reaction is allowed to proceed under normal pressure, although it is also possible to employ a higher or lower pressure.

When the process m) according to the invention is carried out, use is made, for instance, of about 1 to about 1.2 moles, preferably from 1 to about 1.1 moles of the compounds of the formula (XI) per mole of the compounds of the formula (II) for example to obtain the desired compounds of the formula (I).

In carrying out the process n), use is made, as suitable diluent, of any inert solvents such as those exemplified in the above-mentioned process a).

The above mentioned process n) may be carried out in the presence of an acid binder such as exemplified in the process b).

In the process n), the reaction temperature can be varied within a wide range. In general, the reaction is carried out at a temperature of from about 0° to about 150° C., preferably from room temperature to about 80° C. In general, the reaction is allowed to proceed under normal pressure, although it is also possible to employ a higher or lower pressure.

When the process n) according to the invention is carried out, use is made, for instance, of about 1 to about 1.2 moles, preferably from 1 to about 1.1 moles of the compounds of the formula (XIII) per mole of the compounds of the formula (XII) for example in the presence of an inert solvent such as alcohol to obtain the desired compounds of the formula (I).

The active compounds are well tolerated by plants, have a favourable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus Asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera; for example *Blatta orientalis, Periplaneta americana, Leucophaea maderae, Blattella germanica, Acheta domesticus,* Gryllotalpa spp., *Locusta migrato ria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci,* from the order of the Heteroptera, for example Eurygaster spp., *Dysdercus intermedius, Piesma guadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exiqua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiquella, Homona magnanima* and *Tortrix viridana;* from the order of the Coleoptera, for example *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., Melolontha melolontha, Amphimallon solstitialis and *Costelytra zealandica;* from the order of the Hymenoptera for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Aranina, for example Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp..

The plant-parasitic nematodes include Pratylenchus spp., *Radopholus similis, Ditylenchus dipsaci, Tylenchulus semipenetrans*, Heterodera spp., Meloidogyne spp., Aphenlenchoides spp., Longidorus spp., Xiphinema spp., and Trichodorus spp..

Furthermore, in the field of veterinary medicine, the novel compound of the present invention can effectively be employed for combating a variety of noxious animal-parasitic pests (internal- and external-parasitic pests), e.g., parasitic insects and nematodes. Such animal-parasitic pests may be exemplified as follows:

From the class of insects, e.g., Gastrophilus spp., Stomoxys spp., Tricodectes spp., Rhodius spp., *Ctenocephalides canis* and the like.

The active compounds can be converted into the customary formulations, such as solutions, emulsions, wet-table powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins,: clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 per cent by weight of active compound,: preferably from 0.5 to 90 per cent by weight.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agent are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 100% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The preparation and use of the active compounds according to the invention can be seen from the following examples.

EXAMPLES OF PREPARATION

Example 1

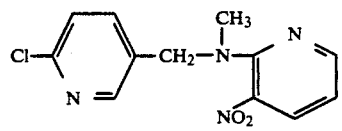

2-chloro-3-nitropyridine (1.59 g), potassium carbonate (1.5 g), and N-(2-chloro-5-pyridylmethyl)-methylamine (1.57 g) were added to dimethylformamide (30 ml) and the resulting mixture was stirred at 80° C. for three hours.

After having been cooled, the reaction solution was poured onto iced water. The separated crude crystals were taken up under filtration and recrystallized from ethanol/ether to obtain the desired 2-[N-(2-chloro-5-pyridylmethyl)-methylamino]-3-nitropyridine (2.1 g) having a melting point in the range from 123° to 124° C.

Example 2

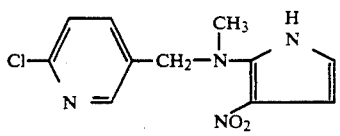

2,2-bis(methylthio)-1-nitroethylene (3.3 g) was dissolved in tetrahydrofuran (100 ml) followed by addition of N-(2-chloro-5-pyridylmethyl)-methylamine (3.2 g) thereto and eight-hours heating under refluxing. After cooling at 50 C., aminoacetal (2.7 g) was added to the resulting solution, followed by eight-hours' stirring at 50° C. After the reaction, tetrahydrofuran in the reaction product was distilled off therefrom under reduced pressure, followed by addition of concentrated hydrochloric acid (50 ml) thereto and overnight stirring at room temperature. The resulting reaction liquid was poured onto 100 ml of iced water and, after extraction with chloroform, was refined with the use of silica gel column chromatography eluant: chloroform/ethanol=15/1) to obtain the desired 2-[N-(2-chloro-5-pyridylmethyl)-N-methylamino]-3-nitropyrrole (0.9 g) having a melting point in the range from 165° to 167° C.

Example 3

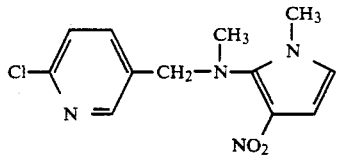

The 2-[N-(2-chloro-5-pyridylmethyl)-N-methylamino]-3-nitropyrrol (0.84 g) that had been obtained in the foregoing Example 2 was dissolved in dimethylformamide (10 ml), followed by addition of a 60% oily sodium hydride (0.13 g) thereto and one-hour stirring at room temperature. Then, dimethyl sulfate (0.4 g) was added to the reaction liquid, followed by five-hours' stirring at 50° C.

After cooling, the reaction liquid was poured onto 30 ml of iced water and, after extraction with methylene chloride, was refined with the use of silica gel column chromatography eluant: chloroform/ethanol=20/1) to obtain the desired 2-[N-(2-chloro-5-pyridylmethyl)-N-methylamino]-1-methyl-3-nitropyrrole (0.7 g) having a melting point in the range from 85° to 89° C.

Example 4

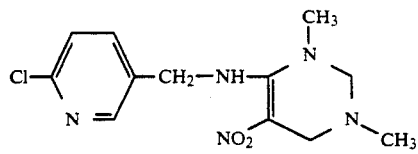

A mixture was subjected to heat-refluxing for two hours, which mixture consisted of 1-(2-chloro-5-pyridylmethylamino)-1-methylamino-2-nitroethylene (1.0 g), methanol solution of methylamine (40%, 0.35 g), aqueous solution of formaldehyde (37%, 0.7 g) and toluene (40 ml).

The solvent was distilled off from the reaction liquid under reduced pressure and the thus obtained residue was refined with column chromatography (eluant: ethanol/chloroform=1:10), to obtain the desired 4-(2-chloro-5-pyridylmethylamino)-1,3-dimethyl-5-nitro-1,2,3,6-tetrahydropyrimidine (0.5 g) having a melting point in the range from 126° to 130° C.

Example 5

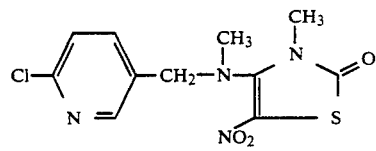

A mixture consisting of 3-methyl-4-methylthio-5-nitro-2-thiazolone (1.0 g), N-(2-chloro-5-pyridylmethyl)-N-methylamine (0.9 g) and ethanol (30 ml) was heat-refluxed for five hours and then cooled to room temperature to obtain the desired 4-[N-(2-chloro-5-pyridylmethyl)-N-methylamino]-3-methyl-5-nitro-2-thiazolone (1.4 g) having a melting point in the range from 147° to 148° C. in a crystal form.

Example 6

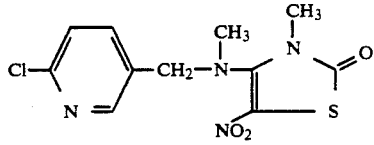

To a mixture of 1-(2-chloro-5-pyridylmethylamino)-1-methylamino-2-nitroethylene (3.0 g) and acetonitrile (30 ml) was added slowly and dropwise chlorocarbonylsulfenyl chloride (1.8 g) at 10° to 20° C. After an overnight stirring, the solvent was distilled off from the reaction liquid under reduced pressure and the thus obtained residue was refined with column chromatography (eluant: ethanol/chloroform=1/10) to obtain the desired 4-[N-(2-chloro-5-pyridylmethyl)-N-methylamino]-3-methyl-5-nitro-2-thiazolone (1.0 g) having a melting point in the range from 147° to 148° C.

Referential Example 1 preparation of material compound of formula (XII)

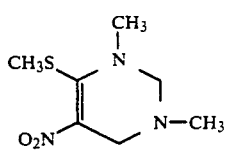

A mixture was subjected to refluxing under heating for two hours, which mixture consisted of 1-methylamino-1-methylthio-2-nitroethylene (3.0 g), methanol solution of methylamine (40%, 1.9 g), aqueous solution of formaldehyde (37%, 4.0 g) and ethanol (50 ml). Under reduced pressure, the solvent was distilled off from the reaction liquid and the thus obtained residue was refined with column chromatography eluant: ethanol/chloroform=1/10) to obtain the desired 1,3-dimethyl-4-methylthio-5-nitro-1,2,3,6-tetrahydropyrimidine (2.6 g) having a melting point in the range from 66°0 to 70° C.

Referential Example 2 preparation of material compound of formula (XII)

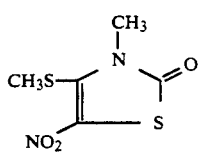

To a mixture of 1-methylamino-1-methylthio-2-nitroethylene (2.0 g) and acetonitrile (30 ml) was added slowly: and dropwise chlorocarbonylsulfenyl chloride (2.5 g) at 10° to 20° C. After an overnight stirring, the resulting crystals were filtered off from the reaction liquid to obtain the desired 3-methyl-4-methylthio-5-nitrothiazolone (2.3 g) having a melting point from 78° to 81° C.

The compounds according to the present invention which can be prepared according to the same method as those employed in the above-mentioned Examples 1 to 5 are shown in the following Table 1, including those that were prepared in the foregoing Examples 1 to 5.

TABLE I

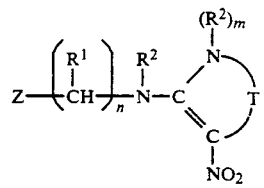

| No. | Z | $R^1$ | n | $R^2$ | $R^3$ | m | Nside T Cside | |
|---|---|---|---|---|---|---|---|---|
| 1 | pyridyl (N=) | H | 1 | H | H | 1 | $-CH_2-\underset{\underset{CH_3}{\mid}}{N}-CH_2-$ | |
| 2 | pyridyl (N=) | H | 1 | H | $CH_3$ | 1 | $-CH_2-\underset{\underset{CH_3}{\mid}}{N}-CH_2-$ | mp. 135-137 °C. |
| 3 | pyridyl (N=) | — | 0 | $CH_2$ | $CH_3$ | 1 | $-CH_2-\underset{\underset{CH_3}{\mid}}{N}-CH_2-$ | |
| 4 | pyridyl (N=) | H | 1 | $CH_3$ | $CH_3$ | 1 | $-CH_2-\underset{\underset{CH_3}{\mid}}{N}-CH_2-$ | |
| 5 | pyrazinyl | H | 1 | H | $CH_3$ | 1 | $-CH_2-\underset{\underset{CH_3}{\mid}}{N}-CH_2-$ | |
| 6 | pyridyl (N=) | H | 1 | H | $C_2H_5$ | 1 | $-CH_2-\underset{\underset{C_2H_5}{\mid}}{N}-CH_2-$ | |

TABLE I-continued $$Z-\left(\underset{CH}{\overset{R^1}{|}}\right)_n - \underset{|}{\overset{R^2}{N}} - \underset{\underset{NO_2}{||}}{\overset{(R^2)_m}{C}} \underset{T}{\overset{N}{\diagdown}}$$

| No. | Z | R¹ | n | R² | R³ | m | Nside T Cside | |
|---|---|---|---|---|---|---|---|---|
| 7 | 6-chloro-3-pyridyl | H | 1 | H | H | 1 | −CH₂−N(CH₃)−CH₂− | |
| 8 | 6-chloro-3-pyridyl | H | 1 | CH₃ | H | 1 | −CH₂−N(CH₃)−CH₂− | mp. 116–121 °C. |
| 9 | 6-chloro-3-pyridyl | H | 1 | CH₃ | CH₃ | 1 | −CH₂−N(CH₃)−CH₂− | mp. 126–130° C. |
| 10 | 6-chloro-3-pyridyl | H | 1 | H | CH₃ | 1 | −CH₂−N(CH₃)−CH₂− | mp. 125–130° C. |
| 11 | 2-chlorothiazol-5-yl | H | 1 | CH₃ | H | 1 | −CH₂−N(CH₃)−CH₂− | |
| 12 | 2-chlorothiazol-5-yl | H | 1 | H | CH₃ | 1 | −CH₂−N(CH₃)−CH₂− | |
| 13 | 2-chlorothiazol-5-yl | H | 1 | CH₃ | CH₃ | 1 | −CH₂−N(CH₃)−CH₂− | |
| 14 | 6-chloro-3-pyridyl | — | 0 | H | CH₃ | 1 | −CH₂−N(CH₃)−CH₂− | |
| 15 | 1,3,4-thiadiazol-2-yl | H | 1 | CH₃ | H | 1 | −CH₂−N(C₃H₇-n)−CH₂− | |
| 16 | 1,3,4-thiadiazol-2-yl | H | 1 | H | CH₃ | 1 | −CH₂−N(CH₃)−CH₂− | |
| 17 | 4-chlorophenyl | H | 1 | H | CH₃ | 1 | −CH₂−N(CH₃)−CH₂− | mp. 131–135° C. |
| 18 | 4-chlorophenyl | H | 1 | CH₃ | H | 1 | −CH₂−N(CH₃)−CH₂− | |

TABLE I-continued

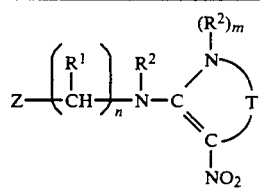

| No. | Z | R¹ | n | R² | R³ | m | Nside T Cside | |
|---|---|---|---|---|---|---|---|---|
| 19 | 4-Cl-C₆H₄ | H | 1 | CH₃ | CH₃ | 1 | $-CH_2-\underset{\underset{CH_3}{\mid}}{N}-CH_2-$ | $n_D^{50}$ 1.6077 |
| 20 | 4-Cl-C₆H₄ | — | 0 | H | CH₃ | 1 | $-CH_2-\underset{\underset{CH_3}{\mid}}{N}-CH_2-$ | |
| 21 | 4-F-C₆H₄ | H | 1 | H | CH₃ | 1 | $-CH_2-\underset{\underset{CH_3}{\mid}}{N}-CH_2-$ | |
| 22 | 3-CN-C₆H₄ | H | 1 | H | CH₃ | 1 | $-CH_2-\underset{\underset{CH_3}{\mid}}{N}-CH_2-$ | |
| 23 | 6-Cl-pyridin-3-yl | CH₃ | 1 | H | CH₃ | 1 | $-CH_2-\underset{\underset{C_2H_5}{\mid}}{N}-CH_2-$ | |
| 24 | 6-Cl-pyridin-3-yl | C₂H₅ | 1 | CH₃ | C₂H₅ | 1 | $-CH_2-\underset{\underset{C_3H_{7}\text{-}n}{\mid}}{N}-CH_2-$ | |
| 25 | 6-Cl-pyridin-3-yl | C₄H₉-n | 1 | H | CH₃ | 1 | $-CH_2-\underset{\underset{C_3H_{7}\text{-}n}{\mid}}{N}-CH_2-$ | |
| 26 | 6-Cl-pyridin-3-yl | CN | 1 | H | CH₃ | 1 | $-CH_2-\underset{\underset{CH_3}{\mid}}{N}-CH_2-$ | |
| 27 | 6-Cl-pyridin-3-yl | CN | 1 | CH₃ | CH₃ | 1 | $-CH_2-\underset{\underset{CH_3}{\mid}}{N}-CH_2-$ | |
| 28 | 6-Cl-pyridin-3-yl | — | 0 | C₃H₇-n | CH₃ | 1 | $-CH_2-\underset{\underset{CH_3}{\mid}}{N}-CH_2-$ | |
| 29 | 6-Cl-pyridin-3-yl | H | 1 | CH₃ | CH₃ | 1 | $-CH_2-\underset{\underset{C_3H_{7}\text{-}n}{\mid}}{N}-CH_2-$ | |

TABLE I-continued

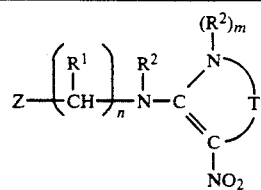

| No. | Z | $R^1$ | n | $R^2$ | $R^3$ | m | Nside T Cside | |
|---|---|---|---|---|---|---|---|---|
| 30 | 6-Cl-pyridin-3-yl | H | 1 | H | $CH_3$ | 1 | $-CH_2-\underset{\underset{C_3H_{7\text{-}iso}}{\mid}}{N}-CH_2-$ | mp. 120–124° C. |
| 31 | 6-Cl-pyridin-3-yl | H | 1 | $CH_3$ | $CH_3$ | 1 | $-CH_2-\underset{\underset{C_3H_{7\text{-}iso}}{\mid}}{N}-CH_2-$ | mp. 120–123° C. |
| 32 | 6-Cl-pyridin-3-yl | H | 1 | H | $CH_3$ | 1 | $-CH_2-N(C_6H_{11})-CH_2-$ (cyclohexyl) | mp. 162–163° C. |
| 33 | 6-Cl-pyridin-3-yl | H | 1 | $CH_3$ | $CH_3$ | 1 | $-CH_2-N(C_6H_{11})-CH_2-$ (cyclohexyl) | |
| 34 | 6-Cl-pyridin-3-yl | H | 1 | H | $CH_3$ | 1 | $-CH_2-\underset{\underset{C_4H_{9\text{-}tert}}{\mid}}{N}-CH_2-$ | mp. 148–150° C. |
| 35 | 6-Cl-pyridin-3-yl | H | 1 | $CH_3$ | H | 1 | $-CH_2-\underset{\underset{C_8H_{17\text{-}n}}{\mid}}{N}-CH_2-$ | |
| 36 | 6-Cl-pyridin-3-yl | H | 1 | H | $CH_3$ | 1 | $-CH_2-\underset{\underset{C_{10}H_{21\text{-}n}}{\mid}}{N}-CH_2-$ | |
| 37 | 6-Cl-pyridin-3-yl | H | 1 | H | $CH_3$ | 1 | $-CH_2-\underset{\underset{C_{12}H_{25\text{-}n}}{\mid}}{N}-CH_2-$ | mp. 101–108° C. |
| 38 | 6-Cl-pyridin-3-yl | H | 1 | $CH_3$ | $CH_3$ | 1 | $-CH_2-\underset{\underset{C_{12}H_{25\text{-}n}}{\mid}}{N}-CH_2-$ | |
| 39 | 6-Cl-pyridin-3-yl | H | 1 | H | $CH_3$ | 1 | $-CH_2-\underset{\underset{C_{14}H_{29\text{-}n}}{\mid}}{N}-CH_2-$ | |
| 40 | 6-Cl-pyridin-3-yl | H | 1 | $CH_3$ | $CH_3$ | 1 | $-CH_2-\underset{\underset{C_{14}H_{29\text{-}n}}{\mid}}{N}-CH_2-$ | |

TABLE I-continued

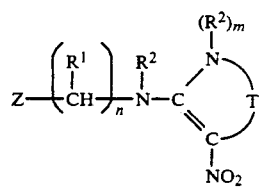

| No. | Z | R¹ | n | R² | R³ | m | Nside T Cside | |
|---|---|---|---|---|---|---|---|---|
| 41 | 2-Cl-pyridin-5-yl | H | 1 | H | $CH_3$ | 1 | $-CH_2-N(CH_2C_6H_5)-CH_2-$ | |
| 42 | 2-Cl-pyridin-5-yl | H | 1 | H | $CH_3$ | 1 | $-CH_2-N(CH_2-C_6H_4-4-F)-CH_2-$ | $n_D^{20}$ 1.6273 |
| 43 | 2-Cl-pyridin-5-yl | H | 1 | $CH_3$ | $CH_3$ | 1 | $-CH_2-N(CH_2-C_6H_4-4-Cl)-CH_2-$ | |
| 44 | 2-Cl-pyridin-5-yl | H | 1 | H | $CH_3$ | 1 | $-CH_2-N(CH_2-(2-Cl-pyridin-5-yl))-CH_2-$ | mp. 193–195° C. |
| 45 | 2-Cl-pyridin-5-yl | H | 1 | $CH_3$ | $CH_3$ | 1 | $-CH_2-N(CH_2-(2-Cl-pyridin-5-yl))-CH_2-$ | $n_D^{50}$ 1.6115 |
| 46 | 2-Cl-pyridin-5-yl | H | 1 | H | $CH_3$ | 1 | $-CH_2-N(CH_2CH_2OCH_3)-CH_2-$ | |
| 47 | pyridin-3-yl | H | 1 | H | $CH_3$ | 1 | $-CH=CH-$ | |
| 48 | 2-Cl-pyridin-5-yl | H | 1 | $CH_3$ | H | 1 | $-CH=CH-$ | mp. 165–167° C. |
| 49 | 2-Cl-pyridin-5-yl | H | 1 | $CH_3$ | $CH_3$ | 1 | $-CH=CH-$ | mp. 85–89° C. |
| 50 | 2-Cl-pyridin-5-yl | H | 1 | $CH_3$ | H | 1 | $-CH=C(CH_3)-$ | |

TABLE I-continued $$Z-(CH(R^1))_n-N(R^2)-C(=C(NO_2)-T)-N(R^2)_m$$

| No. | Z | R¹ | n | R² | R³ | m | Nside T Cside | |
|-----|---|----|----|-----|-----|---|---------------|---|
| 51 | 2-Cl-pyridin-5-yl | H | 1 | CH₃ | — | 0 | =CH—CH=CH— | mp. 123-124° C. |
| 52 | 2-Cl-pyridin-5-yl | H | 1 | CH₃ | — | 0 | =C(Cl)—CH=CH— | mp. 71-74° C. |
| 53 | 2-Cl-pyridin-5-yl | H | 1 | CH₃ | — | 0 | =CH—C(NO₂)=CH— | mp. 106-108° C. |
| 54 | 2-Cl-pyridin-5-yl | H | 1 | CH₃ | — | 0 | =C(N(CH₃)-(6-Cl-pyridin-3-yl))—CH=CH— | Oily |
| 55 | 4-Cl-phenyl | CH₃ | 1 | H | — | 0 | =C(Cl)—C=CH— | mp. 72-74° C. |
| 56 | 4-Cl-phenyl | CH₃ | 1 | H | — | 0 | =C(NHCH(CH₃)-(4-Cl-phenyl))—CH=CH— | Oily |
| 57 | 2-Cl-pyridin-5-yl | H | 1 | C₃H₇-iso | — | 0 | =CH—CH=CH— | mp. 84-86.5° C. |
| 58 | 4-Cl-phenyl | CH₃ | 1 | H | — | 0 | =C(NHCH₂CH₂OC₂H₅)—CH=CH— | mp. 110-115° C. |
| 59 | 2-Cl-pyridin-5-yl | H | 1 | H | CH₃ | 1 | —C(=O)—S— | mp. 176-178° C. |
| 60 | 2-Cl-pyridin-5-yl | H | 1 | CH₃ | CH₃ | 1 | —C(=O)—S— | mp. 147-148° C. |
| 61 | 2-Cl-pyridin-5-yl | H | 1 | H | phenyl | 1 | —C(=O)—S— | mp. 227-228° C. (Decomp.) |

TABLE I-continued

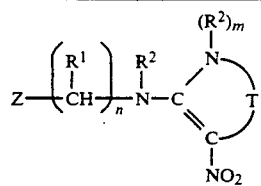

| No. | Z | R¹ | n | R² | R³ | m | Nside T Cside | |
|-----|---|----|----|----|----|---|---------------|---|
| 62 | 2-Cl-pyridin-5-yl | H | 1 | CH₃ | phenyl | 1 | $-\overset{O}{\underset{\|}{C}}-S-$ | mp. 154–155° C. |
| 63 | 2-Cl-pyridin-5-yl | H | 1 | H | 4-tert-C₄H₉-phenyl | 1 | $-\overset{O}{\underset{\|}{C}}-S-$ | mp. 239–241° C. (Decomp.) |
| 64 | 2-Cl-pyridin-5-yl | H | 1 | H | CH₃ | 1 | $-CH=C(C_4H_{9}\text{-}tert)-$ | |
| 65 | 3-methylisoxazol-5-yl | H | 1 | CH₃ | C₂H₅ | 1 | $-CH=CH-$ | |
| 66 | thiazol-5-yl | CH₃ | 1 | H | CH₃ | 1 | $-CH_2-CH_2-$ | |
| 67 | 2-Cl-thiazol-5-yl | H | 1 | H | CH₃ | 1 | $-CH=C(OC_2H_5)-$ | |
| 68 | pyridin-3-yl | H | 1 | C₄H₉-n | CH₃ | 1 | $-\overset{O}{\underset{\|}{C}}-CH_2-$ | |
| 69 | 2-Cl-pyridin-5-yl | H | 1 | H | CH₂CH₂CN | 1 | $-\overset{O}{\underset{\|}{C}}-CH_2-$ | |
| 70 | 2-F-pyridin-5-yl | H | 1 | CH₃ | CH₂CF₃ | 1 | $-\overset{O}{\underset{\|}{C}}-CH(CH_3)-$ | |
| 71 | 2-(pyridin-5-yl)methyl | H | 1 | H | CH₂CH₂OCH₃ | 1 | $-\overset{S}{\underset{\|}{C}}-CH_2-$ | |
| 72 | 5-F-1,3,4-thiadiazol-2-yl | H | 1 | H | CH₃ | 1 | $-\overset{O}{\underset{\|}{C}}-\overset{O}{\underset{\|}{C}}-$ | |
| 73 | 2-Cl-pyridin-5-yl | H | 1 | CH₃ | CH₂ | 1 | $-\overset{O}{\underset{\|}{C}}-\overset{O}{\underset{\|}{C}}-$ | |

TABLE I-continued

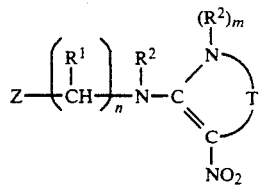

| No. | Z | R¹ | n | R² | R³ | m | Nside T Cside |
|---|---|---|---|---|---|---|---|
| 74 | 6-Cl-pyridin-3-yl | H | 1 | CH$_3$ | CH$_3$ | 1 | −S−C(=O)− |
| 75 | 6-Br-pyridin-3-yl | H | 1 | H | CH$_2$CH=CH$_2$ | 1 | −S−C(=NCOOC$_2$H$_5$)− |
| 76 | 6-Cl-pyridin-3-yl | H | 1 | CH$_3$ | CH$_2$C≡CH | 1 | −S−C(=NCOOCH$_3$)− |
| 77 | 6-F-pyridin-3-yl | H | 1 | CH$_3$ | CH$_3$ | 1 | −N=CH− |
| 78 | 6-Cl-pyridin-3-yl | H | 1 | H | CH$_3$ | 1 | −N=CH− |
| 79 | 6-Cl-pyridin-3-yl | H | 1 | CH$_3$ | CH$_3$ | 1 | −N=CH− |
| 80 | pyridin-3-yl | H | 1 | H | CH$_2$-(4-Cl-phenyl) | 1 | −N=C(OCH$_3$)− |
| 81 | thiazol-5-yl | H | 1 | H | CH$_2$-phenyl | 1 | −N=C(OC$_2$H$_5$)− |
| 82 | phenyl | H | 1 | CH$_3$ | CH$_2$-(6-Cl-pyridin-3-yl) | 1 | −N(CH$_3$)−C(=O)− |
| 83 | 6-Cl-pyridin-3-yl | H | 1 | H | CH$_3$ | 1 | −N=N− |
| 84 | 6-Cl-pyridin-3-yl | — | 0 | H | CH$_3$ | 1 | −CH$_2$−CH$_2$−CH$_2$− |

TABLE I-continued $$Z-(CH(R^1))_n-N(R^2)-C(=C(NO_2))-T-N(R^2)_m-$$

| No. | Z | R¹ | n | R² | R³ | m | Nside T Cside |
|---|---|---|---|---|---|---|---|
| 85 | 6-Cl-pyridin-3-yl | H | 1 | H | C$_4$H$_9$-n | 1 | $-CH_2-C(CH_3)(CH_3)-CH_2-$ (i.e. —CH$_2$—C(H$_3$C)(CH$_3$)—CH$_2$—) |
| 86 | 5-methylpyrazin-2-yl (with 5-CH$_3$) | H | 1 | CH$_3$ | CH$_3$ | 1 | $-CH_2-CH=CH-$ |
| 87 | 3-methylisoxazol-5-yl | H | 1 | H | CH$_3$ | 1 | $-C(=O)-CH=CH-$ |
| 88 | 6-Cl-pyridin-3-yl | H | 1 | C$_2$H$_5$ | CH$_2$-C$_6$H$_5$ | 1 | $-C(=O)-CH=C(COOC_2H_5)-$ |
| 89 | pyrazin-2-yl | H | 1 | H | CH$_2$CH$_2$CN | 1 | $-C(=O)-CH_2-C(=O)-$ |
| 90 | 6-Cl-pyridin-3-yl | CN | 1 | H | CH$_3$ | 1 | $-CH_2-CH_2-C(=NH)-$ |
| 91 | 6-Cl-pyridin-3-yl | H | 1 | H | CH$_3$ | 1 | $-C(=O)-NH-C(=S)-$ |
| 92 | 6-F-pyridin-3-yl | H | 1 | CH$_3$ | C$_2$H$_5$ | 1 | $-C(=O)-N(CH_3)-C(=O)-$ |
| 93 | 6-Cl-pyridin-3-yl | H | 1 | CH$_3$ | H | 1 | $-S-C(=NCH_3)-$ |
| 94 | 6-Cl-pyridin-3-yl | H | 1 | CH$_3$ | H | 1 | $-S-C(=NC_2H_5)-$ |
| 95 | 6-Cl-pyridin-3-yl | H | 1 | H | CH$_3$ | 1 | $-CH_2-N(4-CH_3-C_6H_4)-CH_2-$ |

TABLE I-continued $$Z\underset{}{-}(\underset{R^1}{\overset{}{C}H})_n\underset{R^2}{\overset{}{N}}\underset{}{-}\underset{}{\overset{}{C}}\underset{\overset{}{C}}{\underset{NO_2}{\parallel}}\overset{N(R^2)_m}{\underset{T}{\diagdown}}$$

| No. | Z | $R^1$ | n | $R^2$ | $R^3$ | m | Nside T Cside | |
|---|---|---|---|---|---|---|---|---|
| 96 | 6-Cl-pyridin-3-yl | H | 1 | $CH_3$ | $CH_3$ | 1 | $-CH_2-\underset{C_2H_5}{\overset{|}{N}}-CH_2-$ | |
| 97 | 6-Cl-pyridin-3-yl | H | 1 | H | $CH_3$ | 1 | $-CH_2-\underset{C_3H_{7\text{-}n}}{\overset{|}{N}}-CH_2-$ | mp. 116–117° C. |
| 98 | 6-Cl-pyridin-3-yl | H | 1 | H | $CH_3$ | 1 | $-CH_2-\underset{C_4H_{9\text{-}n}}{\overset{|}{N}}-CH_2-$ | |
| 99 | 6-Cl-pyridin-3-yl | H | 1 | $CH_3$ | $CH_3$ | 1 | $-CH_2-\underset{C_4H_{9\text{-}n}}{\overset{|}{N}}-CH_2-$ | |
| 100 | 6-Cl-pyridin-3-yl | H | 1 | H | $CH_3$ | 1 | $-CH_2-\underset{C_4H_{9\text{-}iso}}{\overset{|}{N}}-CH_2-$ | |
| 101 | 6-Cl-pyridin-3-yl | H | 1 | $CH_3$ | $CH_3$ | 1 | $-CH_2-\underset{C_4H_{9\text{-}iso}}{\overset{|}{N}}-CH_2-$ | |
| 102 | 6-Cl-pyridin-3-yl | H | 1 | H | $CH_3$ | 1 | $-CH_2-\underset{C_4H_{9\text{-}sec}}{\overset{|}{N}}-CH_2-$ | |
| 103 | 6-Cl-pyridin-3-yl | H | 1 | $CH_3$ | $CH_3$ | 1 | $-CH_2-\underset{C_4H_{9\text{-}sec}}{\overset{|}{N}}-CH_2-$ | |
| 104 | 6-Cl-pyridin-3-yl | H | 1 | $CH_3$ | $CH_3$ | 1 | $-CH_2-\underset{C_4H_{9\text{-}tert}}{\overset{|}{N}}-CH_2-$ | |
| 105 | 6-Cl-pyridin-3-yl | H | 1 | H | $CH_3$ | 1 | $-CH_2-\underset{C_5H_{11\text{-}n}}{\overset{|}{N}}-CH_2-$ | |
| 106 | 6-Cl-pyridin-3-yl | H | 1 | $CH_3$ | $CH_3$ | 1 | $-CH_2-\underset{C_5H_{11\text{-}n}}{\overset{|}{N}}-CH_2-$ | |

TABLE I-continued

| No. | Z | R¹ | n | R² | R³ | m | Nside T Cside |
|---|---|---|---|---|---|---|---|
| 107 | 6-Cl-pyridin-3-yl | H | 1 | H | $CH_3$ | 1 | $-CH_2-N(C_6H_{13}\text{-}n)-CH_2-$ |
| 108 | 6-Cl-pyridin-3-yl | H | 1 | $CH_3$ | $CH_3$ | 1 | $-CH_2-N(C_6H_{13}\text{-}n)-CH_2-$ |
| 109 | 6-Cl-pyridin-3-yl | H | 1 | H | $CH_3$ | 1 | $-CH_2-N(C_7H_{15}\text{-}n)-CH_2-$ |
| 110 | 6-Cl-pyridin-3-yl | H | 1 | H | $CH_3$ | 1 | $-CH_2-N(4\text{-}Cl\text{-}C_6H_4)-CH_2-$ |
| 111 | 6-Cl-pyridin-3-yl | H | 1 | $CH_3$ | $CH_3$ | 1 | $-CH_2-N(C_7H_{15}\text{-}n)-CH_2-$ |
| 112 | 6-Cl-pyridin-3-yl | H | 1 | H | $CH_3$ | 1 | $-CH_2-N(C_8H_{17}\text{-}n)-CH_2-$ |
| 113 | 6-Cl-pyridin-3-yl | H | 1 | $CH_3$ | $CH_3$ | 1 | $-CH_2-N(C_8H_{17}\text{-}n)-CH_2-$ |
| 114 | 6-Cl-pyridin-3-yl | H | 1 | H | $CH_3$ | 1 | $-CH_2-N(CH_2CN)-CH_2-$ |
| 115 | 6-Cl-pyridin-3-yl | H | 1 | H | $CH_3$ | 1 | $-CH_2-N(C_6H_5)-CH_2-$ |
| 116 | 6-Cl-pyridin-3-yl | H | 1 | H | $CH_3$ | 1 | $-CH_2-N(3\text{-}Cl\text{-}C_6H_4)-CH_2-$ |

TABLE I-continued

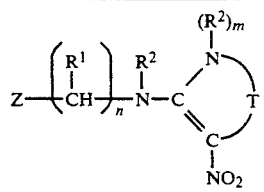

| No. | Z | R¹ | n | R² | R³ | m | Nside T Cside | |
|---|---|---|---|---|---|---|---|---|
| 117 | 6-Cl-pyridin-3-yl | H | 1 | $CH_3$ | $CH_3$ | 1 | $-CH_2-N(4-Cl-C_6H_4)-CH_2-$ | |
| 118 | 6-Cl-pyridin-3-yl | H | 1 | H | $CH_3$ | 1 | $-CH_2-N(4-tert-C_4H_9-C_6H_4)-CH_2-$ | mp. 163–167° C. |
| 119 | 6-Cl-pyridin-3-yl | H | 1 | H | $CH_3$ | 1 | $-CH_2-N(CH_2CH=CH_2)-CH_2-$ | mp. 141–143° C. |
| 120 | 6-Cl-pyridin-3-yl | H | 1 | $CH_3$ | $CH_3$ | 1 | $-CH_2-N(CH_2CH=CH_2)-CH_2-$ | |
| 121 | 6-Cl-pyridin-3-yl | H | 1 | H | $CH_3$ | 1 | $-CH_2-N(CH_2C{\equiv}CH)-CH_2-$ | |
| 122 | 6-Cl-pyridin-3-yl | H | 1 | $CH_3$ | $CH_3$ | 1 | $-CH_2-N(CH_2C{\equiv}CH)-CH_2-$ | |
| 123 | 6-Cl-pyridin-3-yl | H | 1 | H | $CH_3$ | 1 | $-CH_2-N(3,4-Cl_2-C_6H_3-CH_2)-CH_2-$ | mp. 183–185° C. |

Biological Test:

Comparative compounds

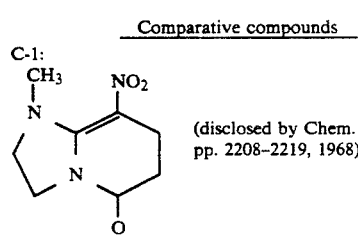

C-1: (disclosed by Chem. Ber., vol. 119, pp. 2208–2219, 1968)

C-2:

-continued
Comparative compounds

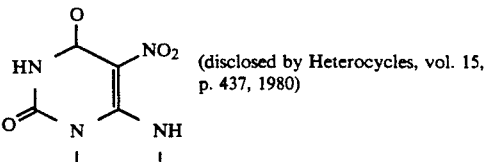

(disclosed by Heterocycles, vol. 15, p. 437, 1980)

EXAMPLE 7

Test on *Mephotettix cincticeps* having resistance to organophosphorus agents:
Preparation of a test chemical Solvent: 3 parts by weight of xylene
Emulsifier: 1 part by weight of polyoxyethylene alkyl phenyl ether To form a suitable preparation, 1 part by weight of the active compound was mixed with the aforesaid amount of the solvent containing the aforesaid amount of the emulsifier. The mixture was diluted with water to a predetermined concentration.

Testing method

Onto rice plants, about 10 cm tall, planted in pots each having a diameter of 12 cm was sprayed 10 ml per pot of the water-dilution of each active compound in a predetermined concentration prepared as above. The sprayed chemical was dried, and a wire net having a diameter of 7 cm and a height of 14 cm was put over each pot, and 30 female imagoes of *Nephotettix cincticeps* showing resistance to organophosphorus agents were released into the net. The pots were each placed in a constant temperature chamber and the number of dead insects was examined 2 days later, and the Insect mortality was calculated.

The results are shown in Table 2.

TABLE 2

| Compound No. | Concentration (ppm) of Active compound | Insect Mortality (%) |
| --- | --- | --- |
| 10 | 200 | 100 |
| 59 | 200 | 100 |
| 60 | 200 | 100 |
| Control | | |
| C-1 | 200 | 0 |
| C-2 | 200 | 0 |

EXAMPLE 8

Test on planthoppers
Testing method

A water dilution in a predetermined concentration of the active compound prepared as in EXAMPLE 7 was sprayed onto rice plants, about 10 cm tall, grown in pots with a diameter of 12 cm in an amount of 10 ml per pot. The sprayed chemical was dried, and a wire net, 7 cm in diameter and 14 cm tall, was put over each of the pots. Thirty female imagoes of *Nilaparvata lugens* Stal of a strain which showed resistance to organophosphorus chemicals were released into the net. The pots were left to stand in a constant temperature chamber and the number of dead insects was examined two days later. The kill ratio was then calculated.

In the same way as above, the insect mortality was calculated on *Sogatella furcifera* Horvath and organophosphoru: resistant *Laodelphax striatellus* Fallen.

The results are shown in Table 3.

TABLE 3

| Compound No. | Concentrations of active compounds ppm | Mortality (%) | | |
| --- | --- | --- | --- | --- |
| | | Nilaparvata lugens | Laodelphax striatellus | Sogatella furcifera |
| 10 | 500 | 100 | 100 | 100 |
| 59 | 500 | 100 | 100 | 100 |
| 60 | 500 | 100 | 100 | 100 |
| Control | | | | |
| C-1 | 500 | 0 | 0 | 0 |
| C-2 | 500 | 0 | 0 | 0 |

It will be appreciated that the instant specification is set forth by way of illustration and not limitation, and that various modifications and changes may be made without departing from the spirit and scope of the present invention.

What is claimed is:

1. A nitro substituted heterocyclic compound of the formula

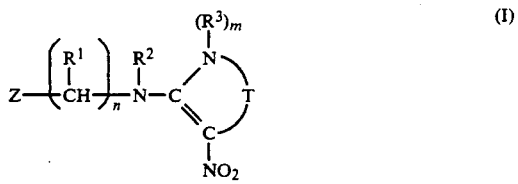

wherein
$R^1$ represents hydrogen, cyano or $C_{1-4}$-alkyl,
m represents 0 or 1,
n represents 0 or 1,
$R^2$ represents hydrogen or $C_{1-4}$-alkyl,
$R^3$ represents hydrogen, $C_{1-16}$-alkyl optionally substituted by halogen,
T completes a ring selected from the group consisting of pyrrole, dihydropyrrole, thiazole, triazole and pyrazole rings optionally substituted by a member selected from the group consisting of $C_{1-14}$ alkyl, $C_{2-4}$ alkenyl, $C_{2-4}$ alkynyl, halogen, $C_{3-7}$-cycloalky, nitro, oxo, thioxo, phenyl optionally substituted by halogen or $C_{1-6}$ alkyl, benzyl optionally substituted by halogen, $C_{1-4}$-alkylmino, $C_{1-4}$alkoxycarbonylimino, N-methyl-N-(2-chloro-5-pyridyl)amino, α-methyl-4-chlorobenzylamino, 2-ethoxy-ethylamino, $C_{1-2}$ alkyl optionally substituted by cyano, $C_{2-4}$ (in total) alkoxyalkyl, 2-chloro-5-pyridylmethyl, $C_{1-4}$ alkoxy, imino, or $C_{1-4}$ alkoxycarbonyl, and
Z represents a thiazole optionally substituted by halogen or $C_{1-4}$ alkyl.

2. A compound according to claim 1,
wherein
$R^1$ represents hydrogen, cyano or methyl,
m represents 0 or 1,
n represents 0 or 1,
$R^2$ represents hydrogen or methyl,
$R^3$ represents hydrogen, methyl, ethyl, propyl, butyl, chloro-or fluoro-substituted $C_{1-4}$-alkyl, alkoxyalkyl having a total of from 2 to 4 carbon atoms, cyano-substituted $C_{1-2}$-alkyl, allyl, propargyl, phenyl which may be substituted by $C_{1-4}$-alkyl or halogen, benzyl which may be substituted by halogen, or pyridylmethyl which may be substituted by halogen,
T completes a ring selected from the group consisting of pyrrole, dihydropyrrole, thiazole, triazole and pyrazole rings optionally substituted by a member selected from the group consisting of methyl, ethyl, propyl, isopropyl, butyl, allyl, propargyl, chlorine, cyclohexyl, nitro, oxo, thioxo, phenyl optionally substituted by chlorine or $C_{1-4}$ alkyl, benzyl optionally substituted by chlorine or fluorine, $C_{1-2}$ alkylmino, $C_{1-2}$ alkoxycarbonylimino, N-methyl-N-(2-chloro-5-pyridyl)amino, α-methyl-4-chlorobenzylamino, 2-ethoxyethylamino, cyanomethyl, 2-methoxyethyl, 2-chloro-5-pyridylmethyl, $C_{1-2}$ alkoxy, imino, or ethoxycarbonyl.

3. A compound according to claim 1, wherein
- $R^1$ represents hydrogen, or methyl,
- m represents 0 or 1,
- n represents 0 or 1,
- $R_2$ represents hydrogen or methyl,
- $R_3$ represents hydrogen, methyl, fluoro-substituted $C_{1-2}$ alkyl, 2-methoxyethyl, 2-cyanoethyl, allyl, propargyl, phenyl, benzyl optionally substituted by chlorine, or 2-chloro-5-pyridylmethyl,
- T completes a ring selected from the group consisting of pyrrole, dihydropyrrole, thiazole, triazole and pyrazole rings optionally substituted by a member selected from the group consisting of methyl, ethyl, propyl, isopropyl, butyl, allyl, propargyl, chlorine, cyclohexyl, nitro, oxo, thioxo, phenyl optionally substituted by chlorine or $C_{1-4}$ alkyl, benzyl optionally substituted by chlorine or fluorine, $C_{1-2}$ alkylimino, $C_{1-2}$ alkoxycarbonylimino, N-methyl-N-(2-chloro-5-pyridyl)amino, α-methyl-4-chlorobenzylamino, 2-ethoxyethylamino, cyanomethyl, 2-methoxyethyl, 2-chloro-5-pyridylmethyl, $C_{1-2}$ alkoxy, imino, or ethoxycarbonyl.

4. An insecticidal composition comprising an insecticidally effective amount of a compound according to claim 1 and an inert diluent.

5. A method of combating insects which comprises applying to such insects or to an insecticidal habitat an insecticidally effective amount of a compound according to claim 1.

* * * * *

UNITED STATES PATENT AND TRADEMARK OFFICE
CERTIFICATE OF CORRECTION

PATENT NO. : 5,219,869
DATED : June 15, 1993
INVENTOR(S) : Shiokawa et al.

It is certified that error appears in the above-identified patent and that said Letters Patent is hereby corrected as shown below:

Col. 48, line 23   After " by " delete " halogen " and substitute -- cyano, halogen or $C_{1-4}$-alkoxy, $C_{3-4}$-alkenyl, $C_{3-4}$-alkynyl, phenyl optionally substituted by $C_{1-4}$-alkyl or halogen, benzyl optionally substituted with halogen or pyridylmethyl optionally substituted by halogen, --

Col. 48, line 32   Delete " $C_{1-4}$-alkylmino " and substitute -- $C_{1-4}$-alkylimino --

Col. 48, lines 62-63   Delete " $C_{1-2}$-alkylmino " and substitute -- $C_{1-2}$-alkylimino --

Signed and Sealed this

Twenty-seventh Day of September, 1994

Attest:

BRUCE LEHMAN

*Attesting Officer*   *Commissioner of Patents and Trademarks*